(12) United States Patent
Heuser et al.

(10) Patent No.: US 12,048,649 B2
(45) Date of Patent: Jul. 30, 2024

(54) OPHTHALMIC PROBE ASSEMBLY WITH FLAT WALL TUBE

(71) Applicant: Alcon Inc., Fribourg (CH)

(72) Inventors: Michael Scott Heuser, Mission Viejo, CA (US); Timothy C. Ryan, Laguna Hills, CA (US); Manish Mahlar Agarkar, Irvine, CA (US); Mark Harrison Farley, Laguna Hills, CA (US)

(73) Assignee: Alcon Inc., Fribourg (CH)

( * ) Notice: Subject to any disclaimer, the term of this patent is extended or adjusted under 35 U.S.C. 154(b) by 316 days.

(21) Appl. No.: 17/643,020

(22) Filed: Dec. 7, 2021

(65) Prior Publication Data

US 2022/0192873 A1 Jun. 23, 2022

Related U.S. Application Data

(60) Provisional application No. 63/127,222, filed on Dec. 18, 2020.

(51) Int. Cl.
| | |
|---|---|
| *A61F 9/008* | (2006.01) |
| *A61B 1/07* | (2006.01) |
| *A61B 17/00* | (2006.01) |
| *A61B 18/20* | (2006.01) |
| *A61B 18/22* | (2006.01) |

(52) U.S. Cl.
CPC ............... *A61F 9/008* (2013.01); *A61B 1/07* (2013.01); *A61B 2017/00867* (2013.01); *A61B 2018/2005* (2013.01); *A61B 2018/208* (2013.01); *A61B 2018/2211* (2013.01); *A61B 2018/2266* (2013.01); *A61F 2009/00863* (2013.01)

(58) Field of Classification Search
CPC ......... A61B 1/0008–00101; A61B 1/07; A61F 9/007–0084
See application file for complete search history.

(56) References Cited

U.S. PATENT DOCUMENTS

| | | |
|---|---|---|
| 1,983,584 A | 12/1934 | Urschel |
| 4,513,601 A | 4/1985 | Herbulot |
| RE33,990 E | 7/1992 | Cudini |
| 5,339,667 A | 8/1994 | Shah et al. |
| 5,638,927 A | 6/1997 | Cheatham et al. |
| 5,855,137 A | 1/1999 | Weber et al. |
| 8,532,456 B2 * | 9/2013 | Hixon ............... A61B 1/00137 385/128 |

(Continued)

FOREIGN PATENT DOCUMENTS

| | | | |
|---|---|---|---|
| JP | H0515550 A | * 1/1993 | |
| WO | WO-2010132751 A1 | * 11/2010 | ......... A61F 9/00727 |

*Primary Examiner* — Mariceli Santiago
(74) *Attorney, Agent, or Firm* — PATTERSON + SHERIDAN, LLP

(57) ABSTRACT

Certain aspects of the present disclosure provide a probe comprising a tube, wherein one or more optical fibers extend at least partially through the tube for transmitting at least one of a laser light and an illumination light from a light source to a target location. A distal end of the tube comprises a flat-walled morphology, and a protective window with a round edge is press-fit to the distal end. The flat-walled morphology of the distal end of the tube has a reduced diametric interference sensitivity, thus allowing a wider range of tolerances between the window and the tube walls for effective press-fitting.

15 Claims, 6 Drawing Sheets

(56) References Cited

U.S. PATENT DOCUMENTS

| | | | |
|---|---|---|---|
| 2004/0158236 A1* | 8/2004 | Thyzel | A61F 9/00736 |
| | | | 606/16 |
| 2009/0275933 A1* | 11/2009 | Zelickson | A61B 18/22 |
| | | | 606/15 |
| 2019/0175273 A1 | 6/2019 | Cook | |
| 2019/0175405 A1 | 6/2019 | Diao | |
| 2019/0175406 A1 | 6/2019 | Cook | |
| 2019/0175408 A1 | 6/2019 | Diao | |

* cited by examiner

OPHTHALMIC PROBE ASSEMBLY WITH FLAT WALL TUBE

PRIORITY CLAIM

This application claims the benefit of priority of U.S. Provisional Patent Application Ser. No. 63/127,222 titled "OPHTHALMIC PROBE ASSEMBLY WITH FLAT WALL TUBE," filed on Dec. 18, 2020, whose inventors are Michael Scott Heuser, Timothy C. Ryan, Manish Malhar Agarkar and Mark Harrison Farley, which is hereby incorporated by reference in its entirety as though fully and completely set forth herein.

FIELD

The present disclosure relates to small-gauge instrumentation for surgical procedures, and more specifically, to a probe assembly for ophthalmic procedures (e.g., vitreoretinal surgery) and the like.

BACKGROUND

Laser and/or illumination probe (e.g., LIP) assemblies may be used during a number of different procedures and surgeries. For example, a laser probe is used during retinal laser surgeries in order to seal retinal tears, among other things. An illumination probe is used to provide illumination to a desired location during performance of a procedure, and may be used in combination with a laser probe. In fact, laser and illumination functions may be carried out by separate probe assemblies, or they may be combined into a single illuminated laser probe assembly. In either case, laser and/or illumination light is typically transmitted from a laser and/or illumination light source through an optical fiber cable. The optical fiber cable proximally terminates in a connector which connects to the light source, and distally terminates in a LIP probe assembly that is manipulated by the surgeon. Note that, herein, a distal end of a component refers to the end that is closer to a patient's body, or where the laser and/or illumination light is emitted out of the probe assembly. On the other hand, the proximal end of the component refers to the end that is facing away from the patient's body or in proximity to, for example, the light source.

The laser and/or illumination probe assembly comprises a hand-piece coupled to a probe tip having a tube that is partly inserted in a patient's eye. The optical fiber cable houses one or more optical fibers that extend through the hand-piece and the tube to transmit laser and/or illumination light onto the patient's retina. In certain cases, a lens is used to magnify and project the light beams propagated by the optical fibers on the patient's retina for increased performance. The lens may be placed into the tube in front of a distal end of the optical fibers.

A protective window is press-fit at a distal end of the tube, thus enclosing the optical fibers and the lens within the tube. The press-fit window protects the optical fibers and the lens by preventing, minimizing, or at least reducing the amount of fluids (e.g., blood) that may leak (e.g., from the patient's body part) into the tube during surgery. The press-fit window may also restrict movement of the lens along the tube and/or prevent the lens from detaching from the tube.

Generally, the distal end of the tube has an annular or round tube shape that matches a morphology of a circular outer wall (e.g., outer edge) of the window to be press-fit therein. However, round tubes have a high diametric interference sensitivity and require very tight tolerances between the tube and window for the tube to remain within its strain limits (e.g., minimum and maximum diametrical interference limits) upon press-fitting. Accordingly, what is needed in the art are improved small-gauge probes for ophthalmic procedures and methods of fabrication thereof.

SUMMARY

The present disclosure relates to laser probe assemblies, and more particularly, to such systems used in surgery (e.g., ophthalmic surgery) and the like.

According to certain embodiments, a probe for ophthalmic procedures is provided. The probe includes a tube having a proximal end and a distal end opposite the proximal end, and an optically clear or transparent window press-fit within the distal end of the tube. The tube further includes one or more optical fibers extending at least partially through the tube for transmitting at least one of a laser light and an illumination light from a light source to a target location. The proximal end of the tube has a single, circumferential outer wall, and the distal end has a plurality of substantially flat outer walls adjoined by at least substantially rounded corners.

According to certain embodiments, a surgical system is provided. The surgical system includes a light source and a probe assembly connected to the light source via one or more optical fibers. The probe assembly further includes a hand-piece connected to a tube, wherein the tube has a proximal end and a distal end opposite the proximal end. An optically clear or transparent window is press-fit within the distal end of the tube. The one or more optical fibers extend through the hand-piece and at least partially through the tube for transmitting at least one of a laser light and an illumination light from the light source to a target location. The proximal end of the tube has a single, circumferential outer wall, and the distal end has a plurality of substantially flat outer walls adjoined by at least substantially rounded corners.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

To facilitate understanding, identical reference numerals have been used, where possible, to designate identical elements that are common to the Figures. It is contemplated that elements and features of one embodiment may be beneficially incorporated in other embodiments without further recitation.

DETAILED DESCRIPTION

In the following description, details are set forth by way of example to facilitate an understanding of the disclosed subject matter. It should be apparent to a person of ordinary skill in the field, however, that the disclosed implementations are exemplary and not exhaustive of all possible implementations. Thus, it should be understood that reference to the described examples is not intended to limit the scope of the disclosure. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Embodiments of the present disclosure generally relate to probes and probe assemblies for ophthalmic procedures having a protective component or window. A probe includes a tube, wherein one or more optical fibers extend at least partially through the tube for transmitting a light from a light source to a target location. A proximal end of the tube may have a single circumferential wall, while a distal end of the tube includes one or more substantially flat outer walls adjoined by at least substantially rounded edges or corners. As described herein, "substantially rounded" refers to round, elliptical, parabolic, or similar smooth curvatures. In certain examples, a lens is housed within the tube at a distal end of the one or more optical fibers. A protective window with a round edge is press-fit to the distal end of the tube, wherein the optional lens may be positioned between the one or more optical fibers and the window. In some embodiments, the substantially rounded corners are positioned to minimize a spring rate of the outer tube walls by maximizing a ratio of bending stress to hoop stress in the outer tube walls. The flat-walled morphology of the distal end of the tube has a reduced diametric interference sensitivity as compared to a round tube morphology, thus allowing a wider range of tolerances between the window's outside diameter and the tube's inner dimensions for effective press-fitting. Accordingly, the reduced diametric interference sensitivity reduces the costs associated with fabrication of small gauge probes, which typically require high precision during press-fitting due to the tight tolerances between tubes and windows required by round tubes.

As used herein, the term "about" may refer to a +/−10% variation from the nominal value. It is to be understood that such a variation can be included in any value provided herein.

Figure 1:
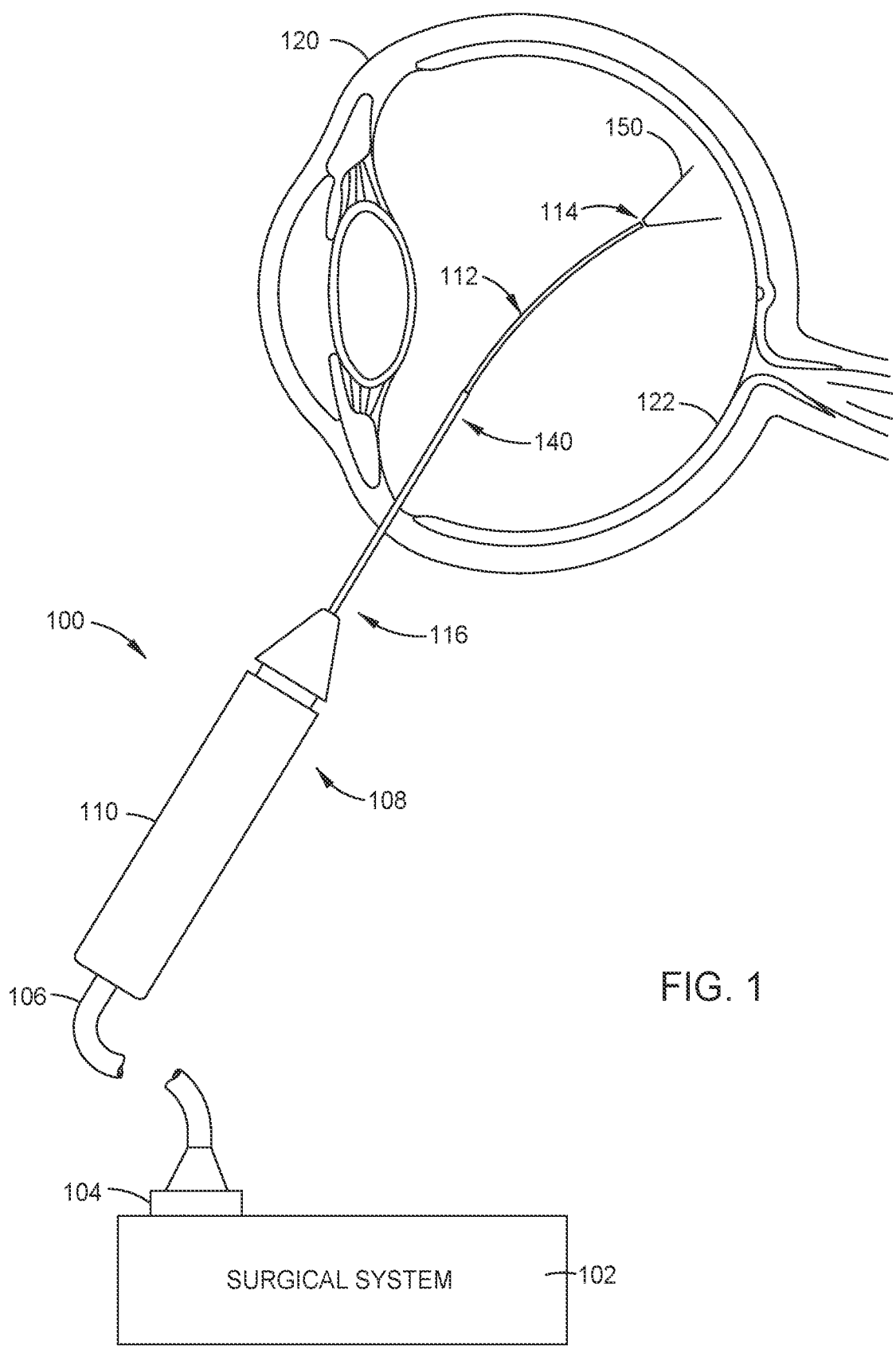
FIG. 1 illustrates an example of a system for generating an illumination light and/or a laser light for delivery to a surgical target, in accordance with certain embodiments of the present disclosure.

FIG. 1 illustrates an example of a system 100 for generating an illumination light and/or a laser light for delivery to a surgical target, according to certain embodiments of the present disclosure. As shown, the system 100 includes a surgical system 102 and a probe 108. The surgical system 102 includes one or more light (e.g., laser and/or illumination light) sources for generating laser light beams and/or illumination light beams that may be used during an ophthalmic procedure. For example, the light sources can alternatively, sequentially, or simultaneously generate a laser light beam and an illumination light beam. A user, such as a surgeon or surgical staff member, can control the surgical system 102 (e.g., via a foot switch, voice commands, etc.) to emit the laser light beam and/or the illumination light beam during an ophthalmic procedure, such as vitreoretinal surgery. In some instances, the surgical system 102 includes a port, and the laser and/or illumination light beams may be emitted from the light sources, through the port, and into an optical fiber cable 106.

System 100 can deliver the laser and/or illumination light beams from the port to the probe 108 via one or more fibers contained in the optical fiber cable 106, a proximal end of which couples to the port through a port adapter 104. As shown, probe 108 includes a hand-piece or probe body 110 and a probe tip 140 having a tube 112 extending an entire length of the probe tip 140. A distal end 114 and a proximal end 116 of the probe tip 140 and thus, of the tube 112, are also depicted in FIG. 1. In operation, a surgeon uses hand-piece 110 to guide tube 112 (e.g., a cylindrical, round hollow tube) into a patient's eye 120. A laser and/or illumination light source of the surgical system 102 generates a light beam 150, which is directed by the tube 112 to a desired location of the eye 120. In certain embodiments, the probe 108 is a multi-spot laser probe and concurrently provides multiple laser light beams 150 resulting in multiple laser spots. Each laser spot's power may be between 150-500 milliwatts (mW) such that by providing multiple laser spots, the minimum power passing through tube 112 is about 1 W. As described above, a lens may be placed in front of the optical fibers in the tube 112 for projecting the laser light beams and/or illumination light beams onto, for example, a patient's eye's retinal surface 122. The proximal ends of the optical fibers, as described above, connect to a laser and/or illumination light source that is coupled to or part of a surgical system.

Aspects described herein relate to the distal end of a probe assembly's tube, wherein a protective window is press-fit. The protective window is placed in front of the distal ends of one or more optical fibers extending through the tube, or in front of the distal end of a lens that is itself placed in front of the distal ends of the one or more optical fibers. The protective window prevents, minimizes, or at least reduces the amount of fluids (e.g., blood) that may leak (e.g., from the patient's body part) into the tube during a procedure, and in embodiments where the probe includes the optional lens described above, may further restrict movement of the lens relative to the tube during surgery.

Figure 2A:
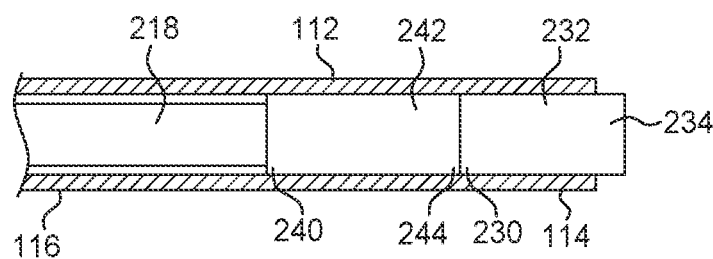
FIGS. 2A-2B illustrate an example tube of the probe assembly of FIG. 1, in accordance with certain embodiments of the present disclosure.

FIG. 2A illustrates a cross-sectional view of an example protective window 232 that is placed at the distal end 114 of tube 112 having optical fiber(s) 218 extending therethrough, according to certain embodiments. As shown, protective window ("window" hereinafter) 232 is placed at distal end 114 of tube 112 while proximal end 116 of tube 112 is connected to a hand-piece (e.g., hand-piece 110 shown in FIG. 1). As described above, distal end 114 of tube 112 is the end that is inserted into the patient's body part, or where laser and/or illumination light is configured to be emitted out of system 100. Tube 112 also includes an optional lens 242, which comprises a proximal end 240 and distal end 244. Further, window 232 comprises a proximal end 230 and distal end 234.

In certain aspects, window 232 comprises an optically clear or transparent material. In certain aspects, the transparent material has optical power and, in certain other aspects, the transparent material does not have optical power. Optical power (also referred to as dioptric power, refractive power, focusing power, or convergence power) is the degree to which a lens, mirror, or other optical system converges or diverges light. Accordingly, the window 232 may itself be a lens, such as a spherical lens having rounded ends 230, 234 or a nonspherical lens having flat ends 230, 234. In certain aspects, window 232 may comprise material that is able to tolerate high temperatures without melting. For example, window 232 may have a transition temperature in the range of 800° C. to 2000° C. Examples of the transparent material include sapphire, fused silica, or other glass or ceramics materials with high transition temperatures.

In certain aspects, window 232 is attached to tube 112 by way of press-fitting of window 232 into the distal end 114 of tube 112. Press-fitting, also known as interference fitting or friction fitting, is a technique for securing window 232 to tube 112, the securing being achieved by the friction between window 232 and tube 112 after window 232 is pushed into tube 112. In certain aspects, the tube 112 is a 23-, 25-, 27-, or 29-gauge tube. For example, the tube 112 may have a gauge of 25 or less. In certain aspects, tube 112 comprises material such as stainless steel, Nitinol (NiTi), a nickel-cobalt-chromium-molybdenum alloy (Ni—Co—Cr—Mo; e.g., MP35N), or a Platinum-iridium alloy (Pt-lr). In certain aspects, window 232, comprises material with enough robustness or rigidity (e.g., hardness or toughness) such that press-fitting window 232 into tube 112 would not result in fracturing window 232, especially when tube 112 is also made of rigid material (e.g. stainless steel). In certain aspects, tube 112 may have an internal dimension (e.g., diameter or width) that is smaller than the diameter of window 232.

As shown, the window 232 partially extends outside of the distal end 114 of tube 112. Although, in certain aspects, window 232 does not extend outside of tube 112. For example, window 232 may be flush with the outside of tube 112, or not extend to the outside of tube 112.

Figure 2B:
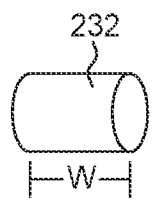

FIG. 2B illustrates a three dimensional view of window 232, according to certain embodiments. As shown, in certain aspects, window 232 is a cylindrical component that is press-fit into an opening in the distal end 114 of tube 112. In certain aspects, the diameter of window 232 may be about 350 µm±5 µm (micrometers), about 360 µm±5 µm, or about 370 µm±5 µm. In certain aspects, a length of window 232, depicted as W in FIG. 2B, may be as long as about 355 µm±25 µm.

As shown in FIGS. 2A and 2B, in certain aspects, a protective window (e.g., 232) may have a cylindrical shape with distal and proximal ends that are both flat. However, in certain aspects, the proximal end of the window is not flat. For example, the proximal end of the window may be spherical or aspheric. In certain embodiments, a window with a spherical or aspheric proximal end is advantageous because a spherical or aspheric proximal end can be more easily guided or inserted through the tip of a tube during press-fitting.

Also, as shown in FIG. 2A, in certain aspects, an optional lens (e.g., lens 242) placed in tube 112 has a cylindrical shape with distal and proximal ends that are both flat. An example of such a lens is a gradient-index (GRIN) lens. However, in certain other aspects, a spherical or aspherical lens is used instead, which may increase the performance and/or thermal reliability of the corresponding probe assembly. As such, in certain aspects, at least one of the proximal or distal ends of the lens is not flat. For example, the proximal, distal, or both ends of the lens may be spherical or aspherical. Note that, any of the different shapes of lenses described herein may be used in conjunction with any of the different shapes of protective components described herein.

Figure 3A:
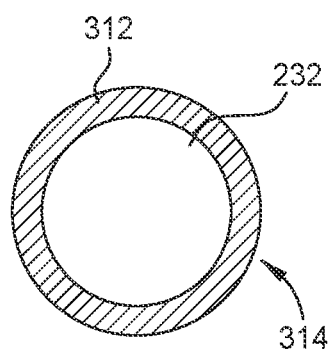
FIGS. 3A-3B illustrate a conventional tube of the probe assembly of FIG. 1, in accordance with certain embodiments of the present disclosure
Figure 3B:
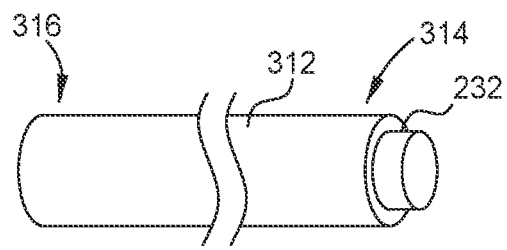

FIGS. 3A and 3B illustrate a cross-sectional front view and a perspective view, respectively, of a conventional tube that is press-fit with window 232. Tube 312 is a hollow, cylindrical tube throughout (e.g., maintains a circular or annular wall along an entire length of the tube), and thus, a distal end 314 of the tube 312 has the same morphology and dimensions as a proximal end 316 of the tube 312. The round, tubular tube 312 has a high diametric interference sensitivity and requires very tight tolerances between the tube 312 and a window, such as window 232, to be effectively press-fit therein. In order to accommodate the required radial displacement when press-fitting the window 232 into the tube 312, the tube 312 undergoes classical hoop strain, which may result in a relatively high average equivalent strain along an inside edge of the tube 312 upon displacement. Accordingly, press-fitting the window 232 within the tube 312 requires precise machining and assembly of the window 232 and tube 312, which can be costly and time-consuming.

Figure 4A:
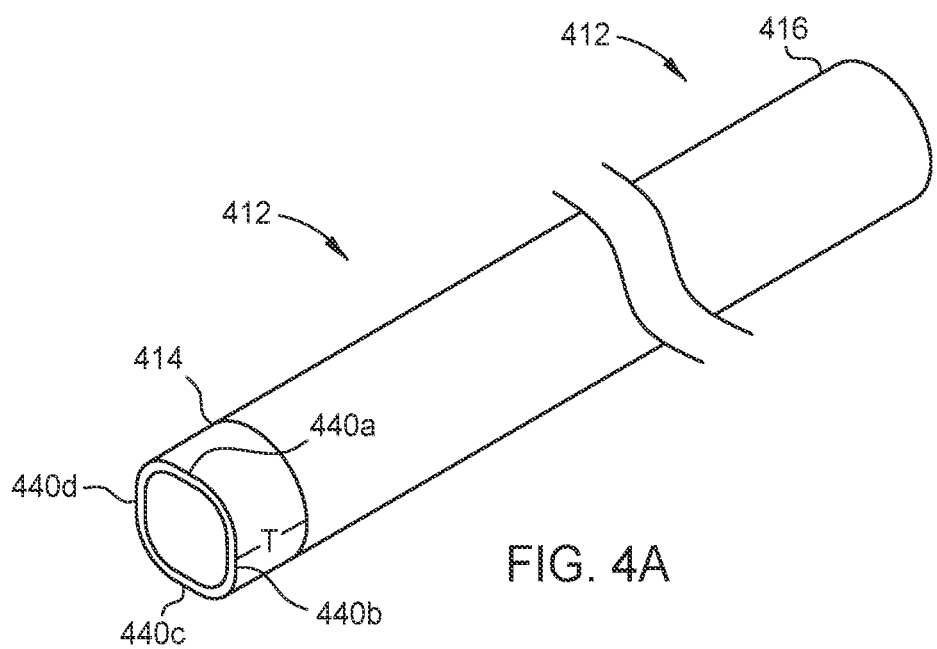
FIGS. 4A-4C illustrate an example tube of the probe assembly of FIG. 1, in accordance with certain embodiments of the present disclosure
Figure 4B:
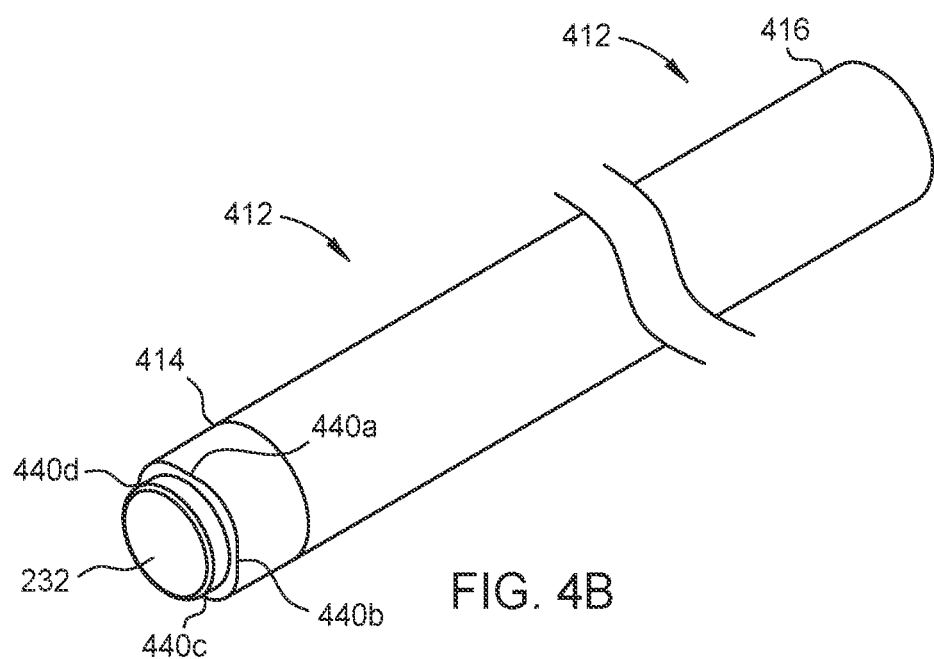
Figure 4C:
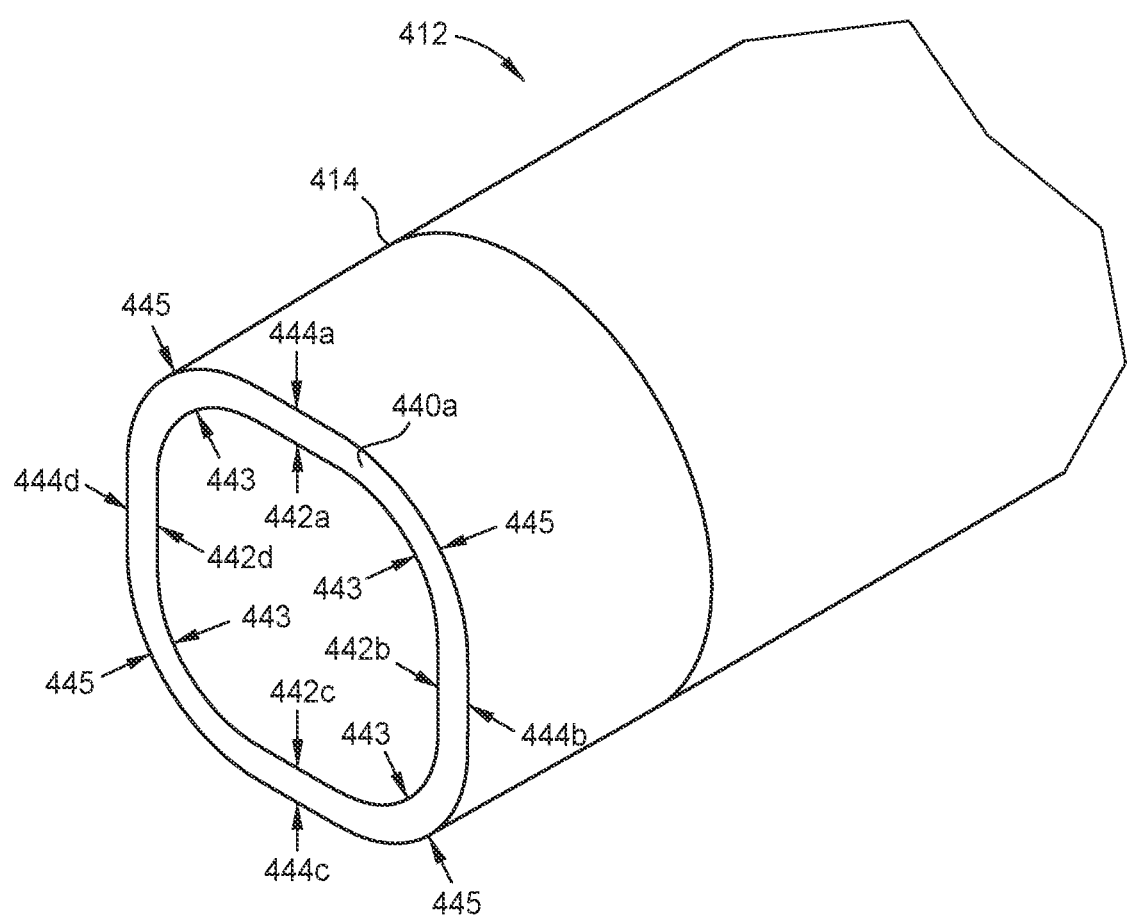

FIGS. 4A-4C illustrate an improved tube that can be press-fit with window 232, according to certain embodiments. FIGS. 4A and 4C illustrate tube 412 prior to being press-fit with window 232, while FIG. 4B illustrates tube 412 having window 232 already press-fit therein.

As shown, tube 412 includes a distal end 414 opposite a proximal end 416. The distal end 414 of the tube 412 is inserted into a patient's body part, such as eye 120, while the proximal end 416 is connected to a hand-piece held by a user, such hand-piece 110. Similar to the tube 312 of FIGS. 3A-3B, the proximal end 416 has a hollow, annular tube-like shape. Unlike the tube 312, however, the distal end of the 414 of the tube 412 includes three or more substantially flat walls 440 (four substantially flat walls 440a-d are shown in FIGS. 4A-4C) connected by at least substantially rounded corners 441 instead of a single, annular wall. For example, the at least substantially rounded corners 441 may have a round, elliptical, parabolic, or similar smooth curvature. In some embodiments, the substantially rounded corners 441 are positioned to minimize a spring rate of the outer walls 440 by maximizing a ratio of bending stress to hoop stress in the outer walls 440. The three or more substantially flat walls 440 have a length T parallel to a major axis of the tube 412 that is substantially equal to at least about 75% of the length W of the window 232 and, in certain embodiments, up to about 200% of the length W of the window 232. Each substantially flat wall 440 further comprises a substantially flat inner edge 442 (four inner edges 442a-d are shown in FIGS. 4A-4C) coupled to adjacent inner edges 442 by inner edge corners 443, and a substantially flat outer edge 444 (four outer edges 444a-d are shown in FIGS. 4A-4C) coupled to adjacent outer edges 444 by outer edge corners 445. Note, that although four flat walls 440a-d are shown, the distal end 414 of tube 412 may include three, five, six, seven, eight, or more walls 440.

The flat-walled morphology of the distal end 414 creates a reduced diametric interference sensitivity as compared to a round-walled morphology, thus enabling a wider range of tolerances for effective press-fitting between an outside diameter of the window 232 and the inner edges 442 of the distal end 414. Accordingly, the average equivalent strain-rate sensitivity along the inner edges 442 and inner edge corners 443 per unit of outward displacement is lower than an average equivalent strain along an inner edge of a round tube, such as tube 312.

Figure 5A:
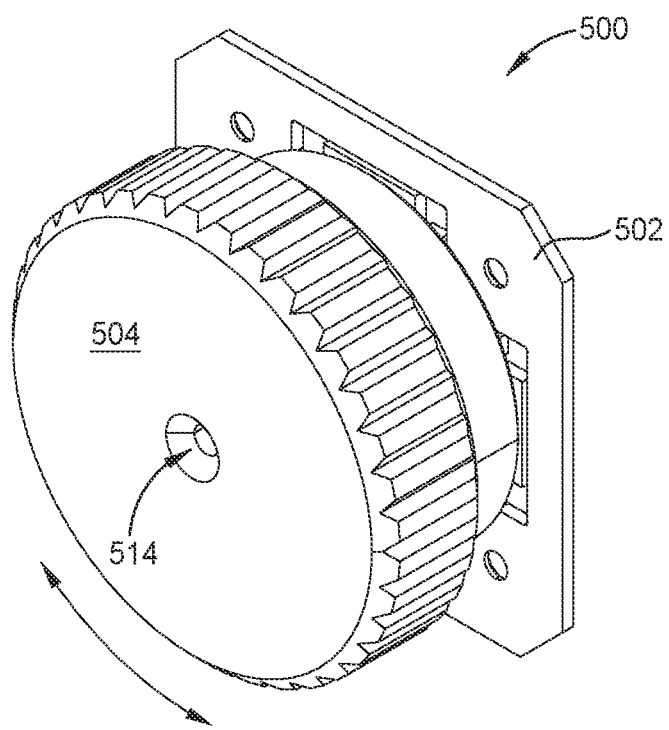
FIGS. 5A-5C illustrate an example pinching device for fabricating the tube of FIGS. 4A-4C, according to certain embodiments of the present disclosure.
Figure 5B:
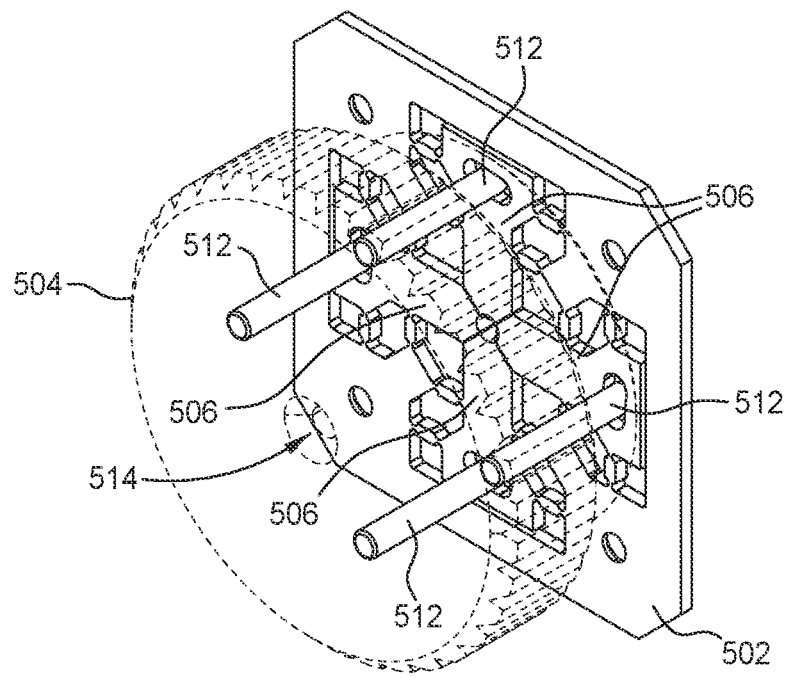
Figure 5C:
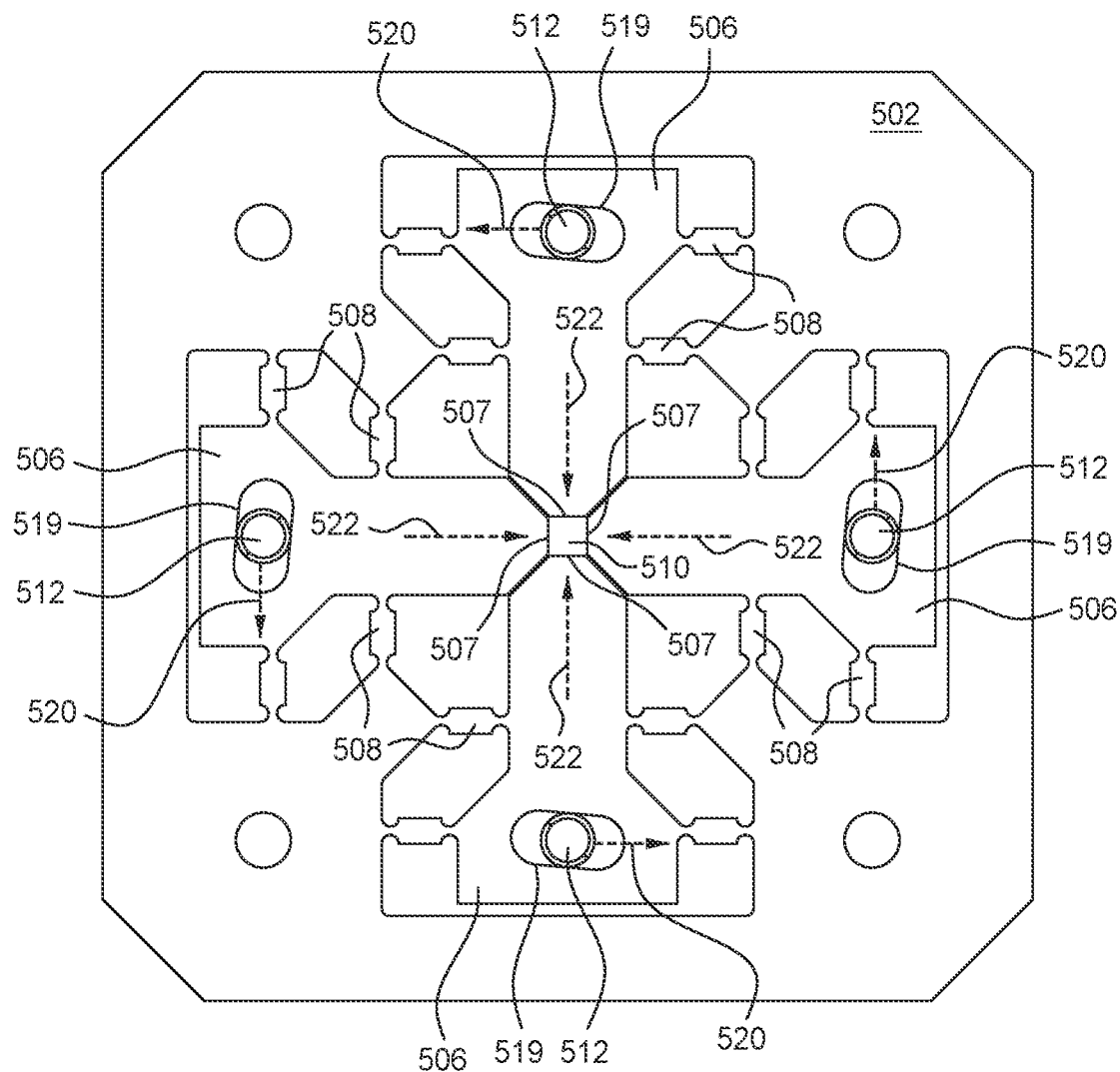

In certain embodiments, the tube 412 is formed by taking a round tube, such as tube 312, and pinching the distal end of the tube at four or more circumferential locations along an outer edge thereof. FIGS. 5A-5C illustrate an example pinching device for fabricating the tube of FIGS. 4A-4C, according to certain embodiments.

As shown, tube pinching device 500 generally includes a base plate 502 and a knob 504 configured to be rotated by a user or a machine. Three or more jaws 506 (four are shown in FIGS. 5B and 5C) are connected to the base plate 502 by flexures 508, which enable radial movement of the jaws 506 relative to the base plate 502. Generally, the number of jaws 506 corresponds to the desired number of flat walls to be formed on the tube. Each of the jaws 506 includes a flat pinching surface 507 (exaggerated in FIG. 5C for purposes of illustration) adjacent a central opening 510 of the base plate 502, and an angled slot 509 at an end opposite the pinching surface 507 through which a dowel pin 512 of the knob 504 is disposed. Each slot 509 is oriented in a manner substantially nonparallel and non-perpendicular to a major axis of the corresponding jaw 506. The knob 504 further includes a central aperture 514 that is aligned with the central opening 510 of the base plate 502 when the knob 504 and the base plate 502 are coupled together.

In operation, a distal end of a round tube, such as tube 312, is inserted through the central aperture 514 of the knob 504 and into the central opening 510 of the base plate 502. A user or machine then rotates the knob, e.g., in a clockwise or counterclockwise direction, causing the dowel pins 512 of the knob 504 to slide within each slot 509 in a tangential direction (represented as arrows 520 in FIG. 5C) relative to the central opening 510. The tangential movement 520 of the dowel pins 512 within the angled slots 509 forces the jaws 506 to translate radially (represented as arrows 522 in FIG. 5C) towards the central opening 510, thus converging the pinching surfaces 507 onto the tube inserted therein at circumferential locations of the tube. As a result, the converging jaws 506 pinch the round wall of the tube into a flat-walled morphology due to the flat pinching surfaces 507, which create a polygon-shaped (e.g., square-shaped in FIG. 5C) aperture when jaws 506 are converged. In certain embodiments, the jaws 506 may converge (e.g., extend inwardly) past desired outer dimensions of the flat-walled tube to account for tube elastic spring-back.

As described above, a probe includes a tube, wherein one or more optical fibers extend at least partially through the tube for transmitting a light from a light source to a target location. A proximal end of the tube may have a single circumferential wall, while a distal end of the tube includes one or more flat outer walls. A protective window with a round edge is press-fit to the distal end of the tube and in front of the one or more optical fibers. The flat-walled morphology of the distal end of the tube has a reduced diametric interference sensitivity as compared to a round tube morphology, thus allowing a wider range of tolerances between the window's outside diameter and the tube's inner dimensions for effective press-fitting. Accordingly, the reduced diametric interference sensitivity reduces the costs associated with fabrication of small gauge probes, which typically require high precision during press-fitting due to the tight tolerances between tubes and windows required by round tubes.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

Within a claim, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for." The word "exemplary" is used herein to mean "serving as an example, instance, or illustration." Any aspect described herein as "exemplary" is not necessarily to be construed as preferred or advantageous over other aspects.

Example Embodiments

Embodiment 1: A surgical system, comprising: a light source; a probe assembly connected to the light source via one or more optical fibers, the probe assembly comprising: a hand-piece connected to a tube, wherein the one or more optical fibers extend through the hand-piece and at least partially through the tube for transmitting at least one of a laser light and an illumination light from the light source to a target location, the tube further comprising: a proximal end have a single, circumferential outer wall; and a distal end opposite the proximal end, the distal end comprising a plurality of substantially flat outer walls adjoined by at least substantially rounded corners; and an optically clear or transparent window press-fit within the distal end of the tube.

Embodiment 2: The surgical system of Embodiment 1 described above, wherein the window is a spherical lens, and wherein at least one of a distal end and a proximal end of the window are curved.

Embodiment 3: The surgical system of Embodiment 1 described above, wherein the window is a nonspherical lens, and wherein a distal end and a proximal end of the window are flat.

Embodiment 4: The surgical system of Embodiment 1 described above, wherein the window comprises at least one of sapphire, fused silica, glass, or ceramic.

Embodiment 5: The surgical system of Embodiment 1 described above, wherein the distal end comprises at least three substantially flat outer walls adjoined by three or more at least substantially rounded corners.

Embodiment 6: The surgical system of Embodiment 5 described above, wherein the distal end comprises at least four substantially flat outer walls adjoined by four or more at least substantially rounded corners.

Embodiment 7: The surgical system of Embodiment 1 described above, further comprising: a lens housed in the tube, the lens positioned between the one or more optical fibers and the window.

Embodiment 8: The surgical system of Embodiment 1 described above, wherein the tube is formed of stainless steel, nitinol, a nickel-cobalt-chromium-molybdenum alloy, or a platinum-iridium alloy.

Embodiment 9: The surgical system of Embodiment 1 described above, wherein the tube has a gauge of 25 or less.

Embodiment 10: The surgical system of Embodiment 1 described above, wherein the probe assembly is a multispot laser probe assembly, and wherein the tube houses one or more optical fibers for propagating laser light.

Embodiment 11: The surgical system of Embodiment 1 described above, wherein the window has an optical power.

Embodiment 12: The surgical system of Embodiment 1 described above, wherein the at least substantially rounded corners have a round, elliptical, or parabolic curvature.

Embodiment 13: The surgical system of Embodiment 1 described above, wherein the substantially rounded corners are positioned to minimize a spring rate of the outer walls by maximizing a ratio of bending stress to hoop stress in the outer walls.

What is claimed is:

1. A probe for ophthalmic procedures, comprising:
   a tube, wherein one or more optical fibers extend at least partially through the tube for transmitting at least one of a laser light and an illumination light from a light source to a target location, the tube further comprising:
      a proximal end having a single, circumferential outer wall; and
      a distal end opposite the proximal end, the distal end comprising a plurality of substantially flat outer walls adjoined by at least substantially rounded corners; and
   an optically clear or transparent window press-fit within the distal end of the tube.

2. The probe of claim 1, wherein the substantially rounded corners are positioned to minimize a spring rate of the outer walls by maximizing a ratio of bending stress to hoop stress in the outer walls.

3. The probe of claim 1, wherein the window comprises a distal end and a proximal end opposite the distal end, and wherein the distal end and the proximal end of the window are connected by a circular outer edge.

4. The probe of claim 3, wherein the window has an optical power.

5. The probe of claim 3, wherein the window is a spherical lens, and wherein at least one of the distal end and the proximal end of the window are curved.

6. The probe of claim 3, wherein the window is a nonspherical lens, and wherein the distal end and the proximal end of the window are flat.

7. The probe of claim 3, wherein the window comprises at least one of sapphire, fused silica, glass, or ceramic.

8. The probe of claim 1, wherein the distal end comprises at least three flat outer walls adjoined by three or more at least substantially rounded corners.

9. The probe of claim 8, wherein the distal end comprises at least four flat outer walls adjoined by four or more at least substantially rounded corners.

10. The probe of claim 1, further comprising:
    a lens housed in the tube, the lens positioned between the one or more optical fibers and the window.

11. The probe of claim 1, wherein the tube is formed of stainless steel, nitinol, a nickel-cobalt-chromium-molybdenum alloy, or a platinum-iridium alloy.

12. The probe of claim 1, wherein the probe is a multispot laser probe, and wherein the tube houses one or more optical fibers for propagating laser light.

13. The probe of claim 1, wherein the at least substantially rounded corners have a round, elliptical, or parabolic curvature.

14. A surgical system, comprising:
    a light source;
    a probe assembly connected to the light source via one or more optical fibers, the probe assembly comprising:
       a hand-piece connected to a tube, wherein the one or more optical fibers extend through the hand-piece and at least partially through the tube for transmitting at least one of a laser light and an illumination light from the light source to a target location, the tube further comprising:
          a proximal end having a single, circumferential outer wall; and
          a distal end opposite the proximal end, the distal end comprising a plurality of substantially flat outer walls adjoined by at least substantially rounded corners; and
       an optically clear or transparent window press-fit within the distal end of the tube.

15. The surgical system of claim 14, wherein the window comprises a distal end and a proximal end opposite the distal end, and wherein the distal end and the proximal end of the window are connected by a circular outer edge.

* * * * *